United States Patent
Drakulic et al.

(10) Patent No.: US 11,843,407 B2
(45) Date of Patent: *Dec. 12, 2023

(54) UNIVERSAL NOTCH FILTER

(71) Applicant: BIOSIG Technologies, Inc., Westport, CT (US)

(72) Inventors: Budimir S. Drakulic, Los Angeles, CA (US); Sina Fakhar, Encino, CA (US); Thomas G. Foxall, Surrey (CA); Branislav Vlajinic, Rochester, MN (US)

(73) Assignee: BioSig Technologies, Inc., Westport, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/084,034

(22) Filed: Dec. 19, 2022

(65) Prior Publication Data
US 2023/0216529 A1 Jul. 6, 2023

Related U.S. Application Data

(63) Continuation of application No. 17/591,008, filed on Feb. 2, 2022, now Pat. No. 11,569,853, which is a
(Continued)

(51) Int. Cl.
*H04B 1/10* (2006.01)
*H04B 1/04* (2006.01)

(52) U.S. Cl.
CPC ......... *H04B 1/1027* (2013.01); *H04B 1/0475* (2013.01); *H04B 2001/1063* (2013.01)

(58) Field of Classification Search
CPC ................ H04B 1/1027; H04B 1/0475; H04B 2001/1063
See application file for complete search history.

(56) References Cited

U.S. PATENT DOCUMENTS

| 4,939,473 A | * 7/1990 | Eno ......................... H03J 7/065 327/558 |
| 5,555,452 A | 9/1996 | Callaway, Jr. et al. |

(Continued)

FOREIGN PATENT DOCUMENTS

WO WO 2016/077145 A1 5/2016

OTHER PUBLICATIONS

International Search Report and Written Opinion of the International Searching Authority directed to related International Patent Application No. PCT/US2020/059372, dated Feb. 18, 2021; 15 pages.
(Continued)

*Primary Examiner* — Kabir A Timory
(74) *Attorney, Agent, or Firm* — Sterne, Kessler, Goldstein & Fox. P.L.L.C.

(57) ABSTRACT

Systems, methods, and computer program product embodiments are disclosed for removing any fixed frequency interfering signal from an input signal without introducing artifacts that are not part of the original signal of interest. An embodiment operates by using a virtual buffer with a length that matches a length of one cycle of an interfering signal. The embodiment extracts the interfering signal into the virtual buffer. For a sample in the next cycle of the interfering signal that corresponds to a virtual memory location for the virtual buffer, the embodiment can update one or more physical memory locations of the virtual buffer that are in the vicinity of the virtual memory location. This use of virtual buffer can remove any interfering signal without creating the artifacts associated with conventional notch filters.

20 Claims, 12 Drawing Sheets

Related U.S. Application Data continuation of application No. 17/091,357, filed on Nov. 6, 2020, now Pat. No. 11,265,031.

(60) Provisional application No. 62/933,020, filed on Nov. 8, 2019.

(56) References Cited

U.S. PATENT DOCUMENTS

| | | |
|---|---|---|
| 6,498,820 B1 | 12/2002 | Thomson |
| 7,656,933 B2 | 2/2010 | Klinke et al. |
| 2004/0003199 A1 | 1/2004 | May et al. |
| 2011/0040200 A1 | 2/2011 | Douglas et al. |
| 2012/0087406 A1 | 4/2012 | Lim et al. |
| 2013/0072143 A1 | 3/2013 | Dabiri |
| 2015/0303956 A1* | 10/2015 | Kroeger ............ H04B 1/109 375/350 |
| 2021/0143851 A1 | 5/2021 | Drakulic et al. |
| 2022/0263528 A1 | 8/2022 | Drakulic et al. |

OTHER PUBLICATIONS

International Preliminary Report on Patentability directed to the related International Patent Application No. PCT/US2020/059372, dated May 10, 2022.

Furno, Gregory S. et al., "A Learning Filter for Removing Noise Interference," IEEE Transactions on Biomedical Engineering, vol. BME-30, No. 4, Apr. 1983, pp. 234-235. Downloaded Feb. 18, 2021.

Anonymous, "Data Buffer—Wikipedia" Jun. 4, 2013, retrieved from the Internet: URL: https://en.wikipedia.org/w/index.php?title=Data_buffer&oldid=558302874. Downloaded Feb. 18, 2021.

Woo, J. et al., "Improved Noise Reduction in Single Fiber Auditory Neural Responses Using Template Subtraction," J. of Neuroscience Methods, Elsevier Science Publisher, vol. 155, No. 2, Sep. 15, 2006, pp. 319-327; Downloaded Feb. 22, 2021.

Bazhyna, A. et al., "Powerline Interference Suppression in High-Resolution ECG," Computers in Cardiology 2003; 30:561-64. Downloaded Feb. 18, 2021.

\* cited by examiner

UNIVERSAL NOTCH FILTER

CROSS-REFERENCE TO RELATED APPLICATIONS

This application is a continuation of U.S. patent application Ser. No. 17/591,008, filed Feb. 2, 2022, now allowed, which is a continuation of U.S. patent application Ser. No. 17/091,357, filed Nov. 6, 2020, now U.S. Pat. No. 11,265, 031, which claims priority to U.S. Provisional Patent Application titled "Universal Notch Filter," Ser. No. 62/933,020, filed Nov. 8, 2019, which are all incorporated herein by reference in their entirety.

BACKGROUND

There are many situations where an input signal is contaminated with an interfering signal. For example, this may occur in a medical lab in which numerous pieces of equipment secondarily emit substantial line frequencies and propagating harmonics noise. For example, in North America this often involves 60 Hz line frequencies and harmonics thereof. Moreover, there may be interfering signal emissions from other equipment related to their operating frequencies and duty cycles. To accurately display and or record signal(s) of interest from various sources, such as a patient underdoing a medical procedure, there is often a need to remove any fixed frequency interfering signal while preserving the signal(s) of interest. Specifically, there is often a need to remove any fixed frequency interfering signal without introducing artifacts (e.g., overshoot and ringing) that are not part of the original signal(s) of interest.

BRIEF DESCRIPTION OF THE DRAWINGS

The accompanying drawings, which are incorporated herein and form part of the specification, illustrate the present embodiments and, together with the description, further serve to explain the principles of the present embodiments and to enable a person skilled in the relevant art(s) to make and use the present embodiments.

Figure 1:
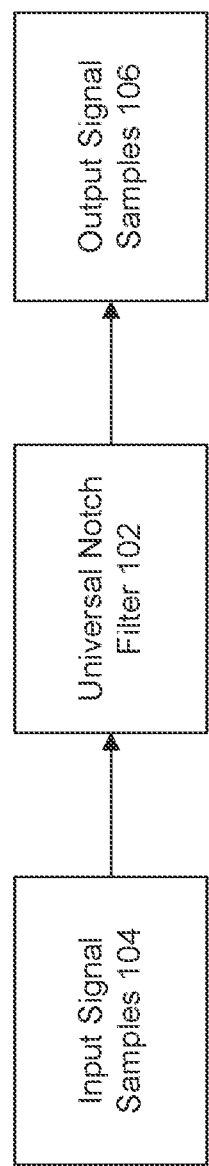
FIG. 1 is a block diagram of a universal notch filter that removes any fixed frequency interfering signal from a signal of interest without introducing artifacts that are not part of the original signal, according to some embodiments.

The features and advantages of the present embodiments will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

Provided herein are system, apparatus, device, method and/or computer program product embodiments, and/or combinations and sub-combinations thereof, for removing any fixed frequency interfering signal from an input signal without introducing artifacts (e.g., overshoot and ringing) that are not part of the original signal of interest.

There are many situations where an input signal is contaminated with an interfering signal. For example, this may occur in a medical lab in which numerous pieces of equipment tend to emit noise having substantial line frequencies and propagating harmonics. For example, in North America this primarily involves 60 Hz line frequencies plus harmonics. Moreover, there may be interfering signal emissions from other equipment related to their operating frequencies and duty cycles. To accurately display and or record signals of interest from various sources, there is often a need to remove any interfering signal from an input signal while preserving the original signal of interest.

Conventional solutions for removing interference of a fixed frequency signal while preserving the signal of interest suffer from several technological problems. First, these conventional solutions often introduce artifacts (e.g., overshoot and ringing) that are not part of the original signal of interest. Second, these conventional solutions are often unable to remove multiple harmonics of any interfering signal. Finally, these conventional solutions often cannot calculate the frequency of an interfering signal in real time, or dynamically remove the interfering signal in real time. Systems, methods, and computer program products for accurately displaying and or recording signals of interest (e.g., biomedical signals such as electrocardiography signals) from various sources is detailed in U.S. Pat. No. 10,356,001, titled "Systems And Methods To Visually Align Signals Using Delay," which is incorporated herein by reference in its entirety.

Embodiments described in this disclosure solve these technological problems. For example, FIG. 1 is a block diagram of a universal notch filter 102 that removes any fixed frequency interfering signal from an input signal without introducing artifacts (e.g., overshoot and ringing) that are not part of the original signal of interest, according to some embodiments. An input signal can be a combination of a signal of interest and an interfering signal. A fixed frequency interfering signal can be an interfering signal having a fixed frequency. A fixed frequency interfering signal can also be an interfering signal having a frequency that varies by approximately 1% over a fixed time period, including, but not limited to, a period of one minute. Universal notch filter 102 can receive samples of the input signal (e.g., input signal samples 104). Universal notch filter 102 can then output samples of the input signal with the interfering signal removed (e.g., output signal samples 106).

Universal notch filter 102 can be hardware or firmware circuitry, software or sub-combinations thereof. For example, universal notch filter 102 can be a software module capable of being executed by a processor (or processors) such as processor 1204 in FIG. 12. Universal notch filter 102 can apply a digital processing function to one or more signal samples. As would be appreciated by a person of ordinary skill in the art, a digital processing function may be a mathematical algorithm that takes one or more signal samples as input, processes them, and produces one or more potentially modified signal samples as output. A digital processing function may be implemented using one or more mathematical operations such as a fast Fourier transform, wavelets, or the like. As would be appreciated by a person of ordinary skill in the art, universal notch filter 102 can apply various types of digital processing functions.

Figure 2:
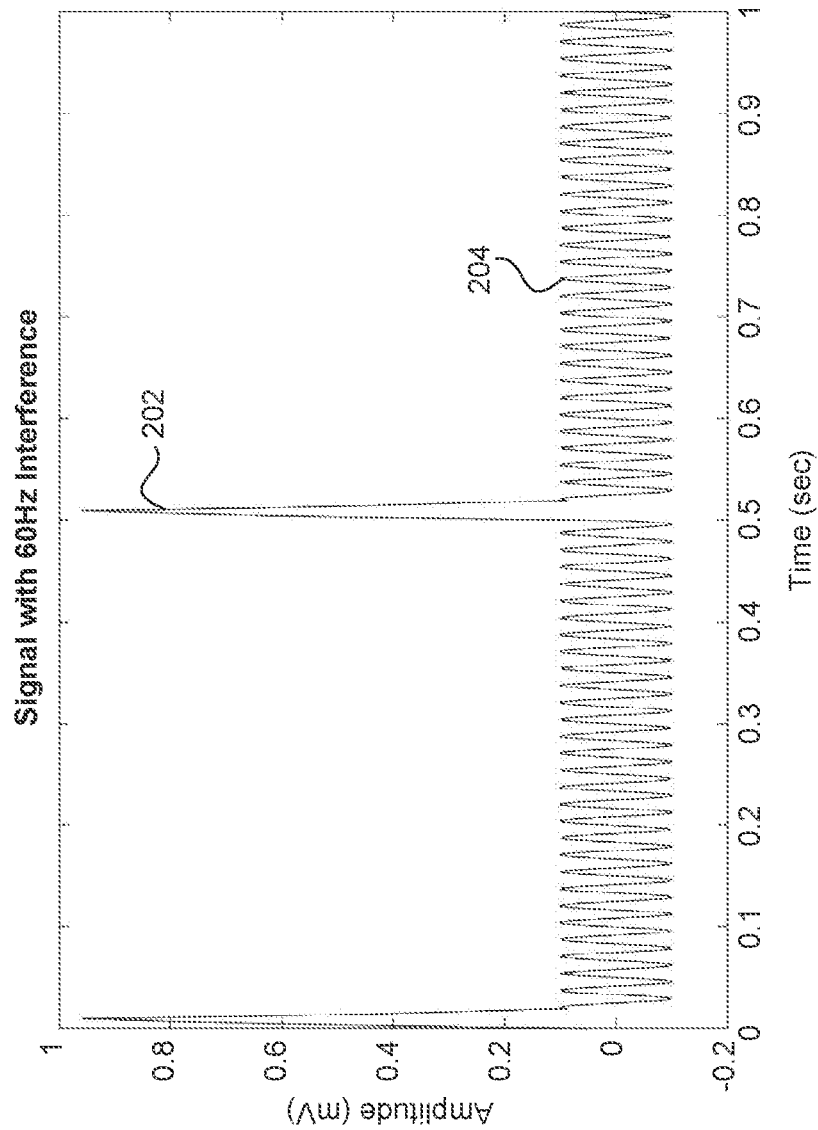
FIG. 2 illustrates an example of an input signal with superimposed interfering signal.

Universal notch filter 102 can remove any fixed frequency interfering signal from an input signal without introducing artifacts (e.g., overshoot and ringing) that are not part of the original signal of interest. For example, an electrocardiography signal may be contaminated with noise in a electrophysiology lab with numerous pieces of equipment that emit substantial line frequencies and harmonics (e.g., noise at one or more frequencies). For example, in North America, this can be primarily a 60 Hz noise signal plus harmonics noise. FIG. 2 illustrates an example of a signal (e.g., spikes 202) with superimposed 60 Hz interfering signal 204, according to some embodiments.

Figure 3:
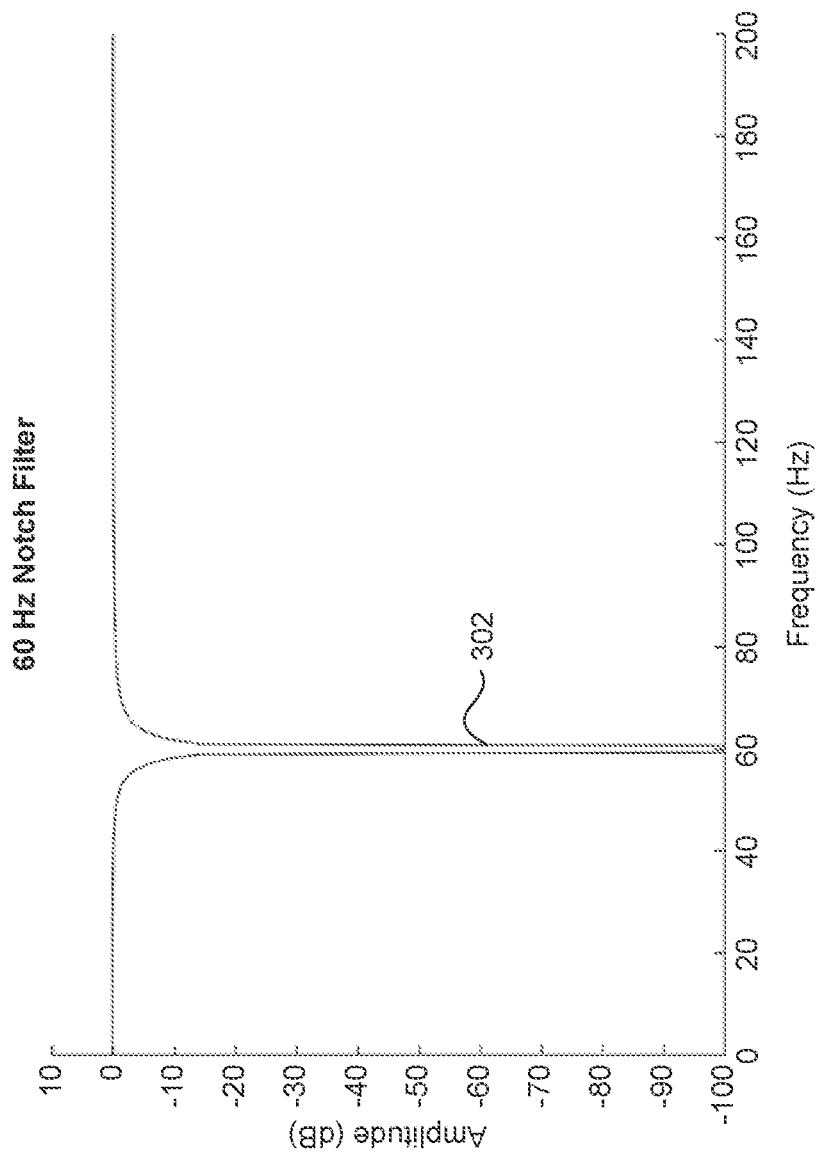
FIG. 3 illustrates an example of a conventional approach to removing noise using a notch filter.

It is desirable to remove an interfering signal while preserving the signal of interest. For example, this is often the case when attempting to accurately record cardiac signals of interest during heart mapping, ablation or other similar medical procedures. Conventional solutions to removing a 60 Hz interfering signal involve using a notch filter with a transmission zero at 60 Hz. FIG. 3 illustrates an example of a conventional approach to removing a 60 Hz interfering signal using a notch filter with a transmission zero (a single notch) 302 at 60 Hz.

Figure 4:
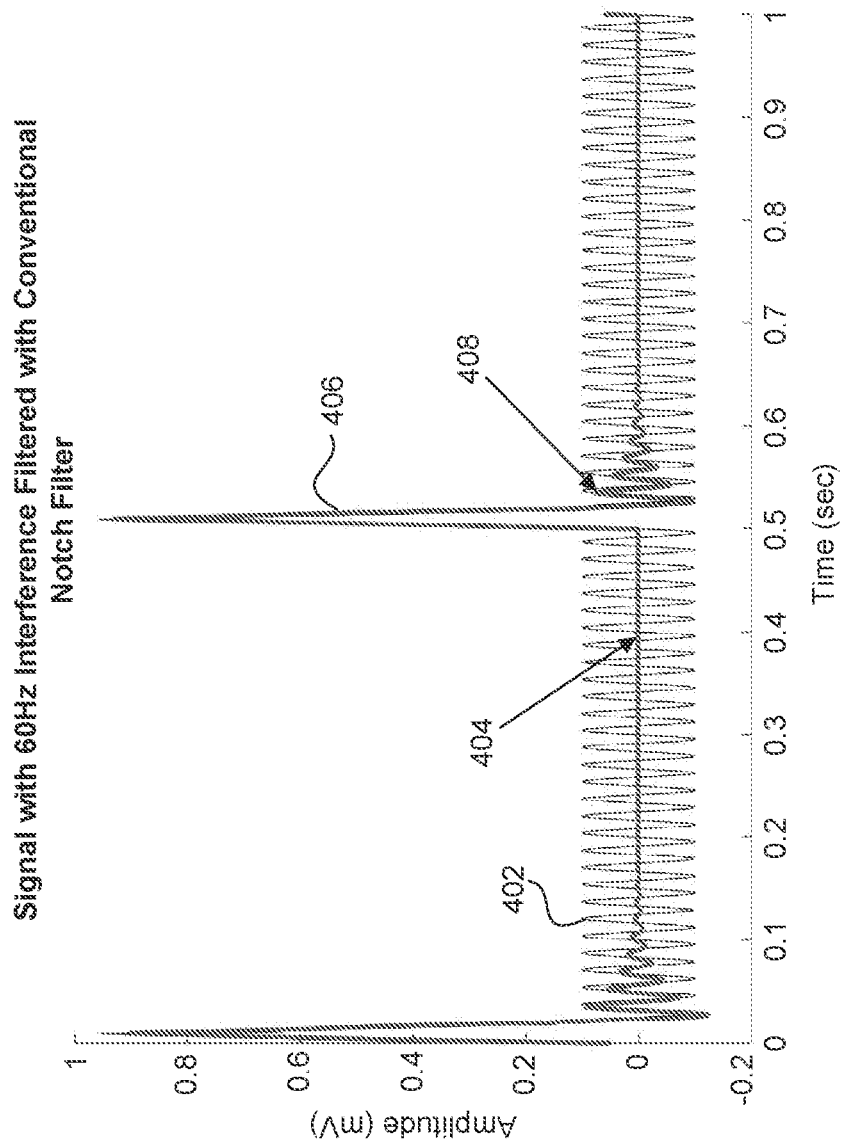
FIG. 4 illustrates an example of the result of applying the conventional notch filter of FIG. 3.

FIG. 4 illustrates an example of the result of applying the notch filter of FIG. 3. As shown in FIG. 4, the 60 Hz interfering signal is removed from the input signal 402 to produce the filtered signal 404. However, the notch filter of FIG. 3 can suffer from several technological problems. For example, after a large spike 406, the notch filter of FIG. 3 can introduce transient responses like overshoot and ringing 408 into the filtered signal 404. This overshoot and ringing can be an artifact of the filter and not part of the original input signal of interest. This is undesirable in many applications, for example, in electrophysiology applications, which can result in less accurate cardiac recordings because of such overshoot and ringing.

Figure 5:
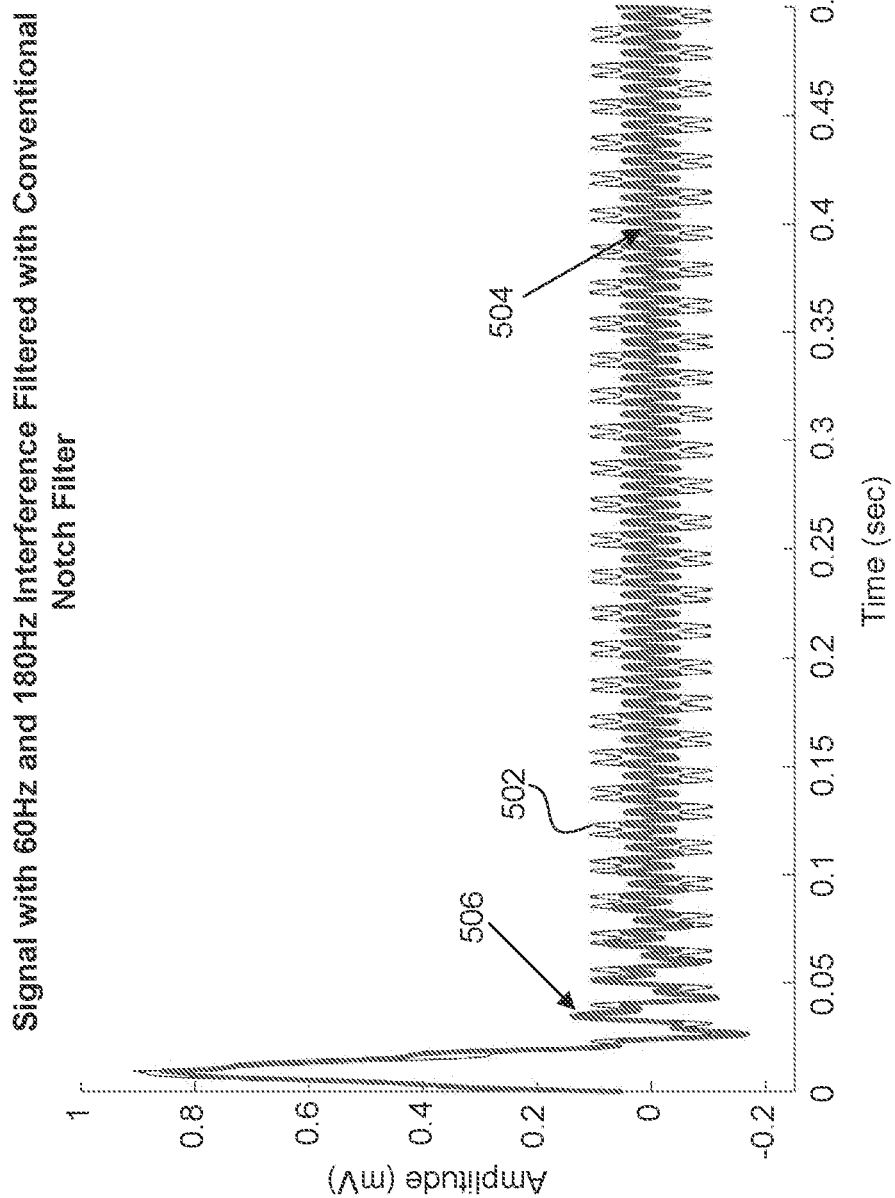
FIG. 5 illustrates an example of a 180 Hz harmonic still present at the output of the conventional notch filter of FIG. 3.

In addition, a conventional 60 Hz notch filter may not reduce any of the harmonics of the 60 Hz interfering signal. For example, as illustrated in FIG. 5, if the input signal 502 includes both 60 Hz and 180 Hz interfering signals, the 180 Hz harmonic can still be present at the output of the conventional notch filter. FIG. 5 illustrates an example of the 180 Hz harmonic still present in the filtered signal 504 at the output of the conventional filter of FIG. 3.

Thus, conventional notch filters can suffer from several technological problems. First, conventional notch filters can introduce overshoot and ringing into a signal of interest. Second, conventional notch filters are often unable to remove multiple harmonics of any interfering signal. Finally, conventional notch filters often cannot calculate the frequency of an interfering signal in real time, or dynamically remove the interfering signal in real time.

In some embodiments, universal notch filter 102 can apply a notch filter that does not introduce overshoot and ringing into a signal of interest, reduces higher-level harmonics, removes any fixed frequency interfering signal, and has an adjustable convergence time. Universal notch filter 102 can solve the above technological problems of conventional notch filters by using a virtual buffer with a length that matches the length of one cycle of the interfering signal. Universal notch filter 102 can extract the interfering signal into the virtual buffer and subtract it from the input signal. This can remove the interfering signal without creating the artifacts associated with conventional notch filters (e.g., overshoot and ringing).

A virtual buffer can be a data buffer managed by software. The virtual buffer can be a circular data buffer. Universal notch filter 102 can set the length of the virtual buffer to a length that matches the length of one cycle of an interfering signal. In other words, the frequency of the interfering signal can determine the time interval of the virtual buffer.

The virtual buffer can be implemented using one or more physical memory locations that store data (e.g., samples of a signal). The number of physical memory locations of the virtual buffer can determine the accuracy of the representation of the interfering signal cycle in the virtual buffer.

The virtual buffer can present a finite number of virtual memory locations. A virtual memory location in the virtual buffer can correspond to a physical memory location. A virtual memory location may also not correspond to a single physical memory location. For example, universal notch filter 102 can store data (e.g., samples of a signal) corresponding to a virtual memory location in the virtual buffer that does not have a corresponding single physical memory location by updating one or more physical memory locations that are in the vicinity of the virtual memory location. Thus, the virtual buffer can provide one or more virtual memory locations to store data (e.g., samples of a signal), where a virtual memory location can correspond to either a physical memory location or a non-physically addressable memory location that is implemented using one or more physical memory locations.

To determine the length to set the virtual buffer, universal notch filter 102 can calculate the frequency of the interfering signal in real time (e.g., using Fast Fourier Transform or other techniques). Universal notch filter 102 can then set the length of the virtual buffer to match the length of one cycle of the interfering signal.

Universal notch filter 102 can also adjust the cycle length of the virtual buffer to match a change in cycle length of the interfering signal. This can involve universal notch filter 102 checking for a movement of the stored interfering signal in the virtual buffer. For example, when the number of discrete locations for the virtual buffer perfectly matches the interfering signal cycle length, the stored interfering signal pattern can be stationary in the virtual buffer. But if the virtual buffer length is too long, the pattern can move to the left. If it is too short, the pattern can move to the right. Universal notch filter 102 can adjust the length for the virtual buffer to match the cycle length of the interfering signal in the input signal by determining the speed and direction of the pattern shift.

Figure 6:
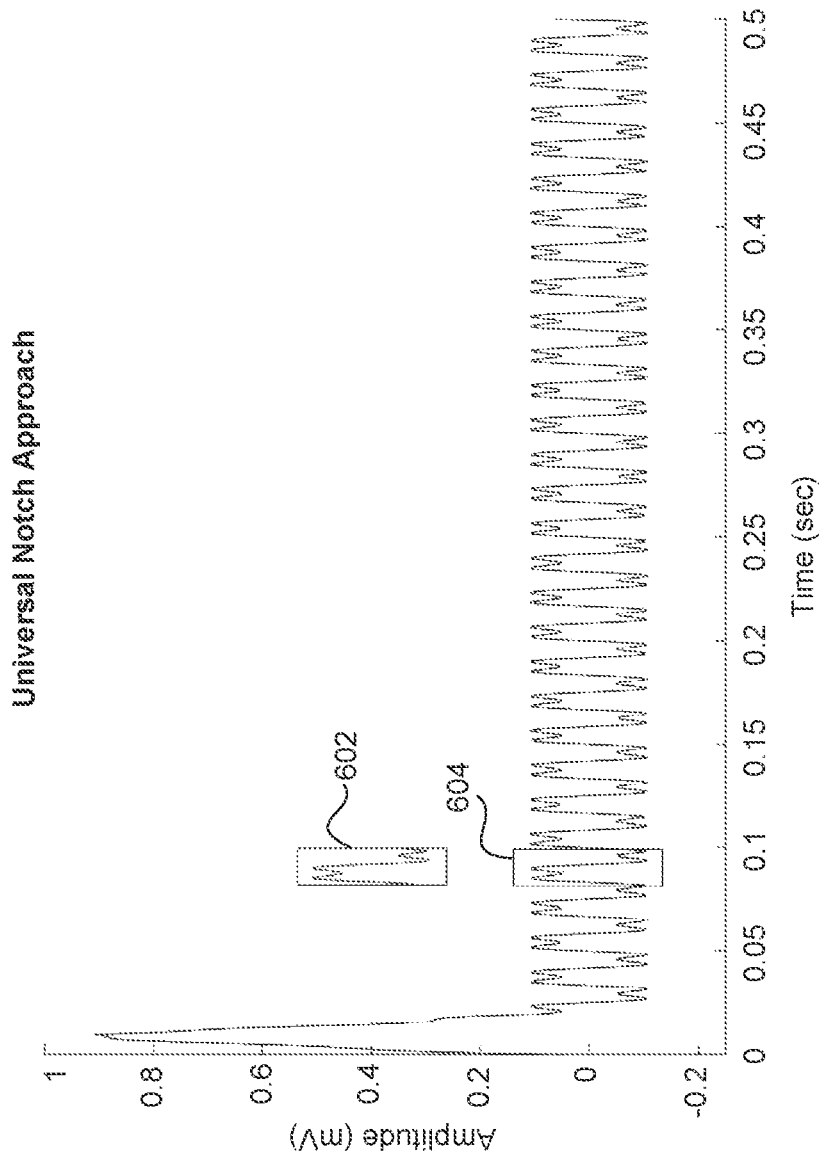
FIG. 6 illustrates an example of a universal notch filter that filters a signal with 60 Hz and 180 Hz interfering signals, according to some embodiments.

In some embodiments, where the frequency of the interfering signal is known ahead of time, universal notch filter 102 can reproduce one cycle of the interfering signal in the virtual buffer and subtract it from the input signal to extract the original signal of interest. Since the line frequency noise can be constant or nearly constant, universal notch filter 102 can use some variation of averaging to refine the estimate over time. Because the frequency of the interfering signal is known ahead of time, the virtual buffer length can be predetermined. In addition, if the virtual buffer is configured to store exactly one cycle, the virtual buffer can also store an integral number of higher frequency harmonics which can be subtracted from the input signal. FIG. 6 illustrates an example of using universal notch filter 102 to filter an interfering signal with 60 Hz and 180 Hz noise, according to some embodiments. Because the line frequency noise is constant, one cycle of interference 602 can be reproduced and subtracted from each cycle 604 of consecutive cycles in the input signal.

Figure 7:
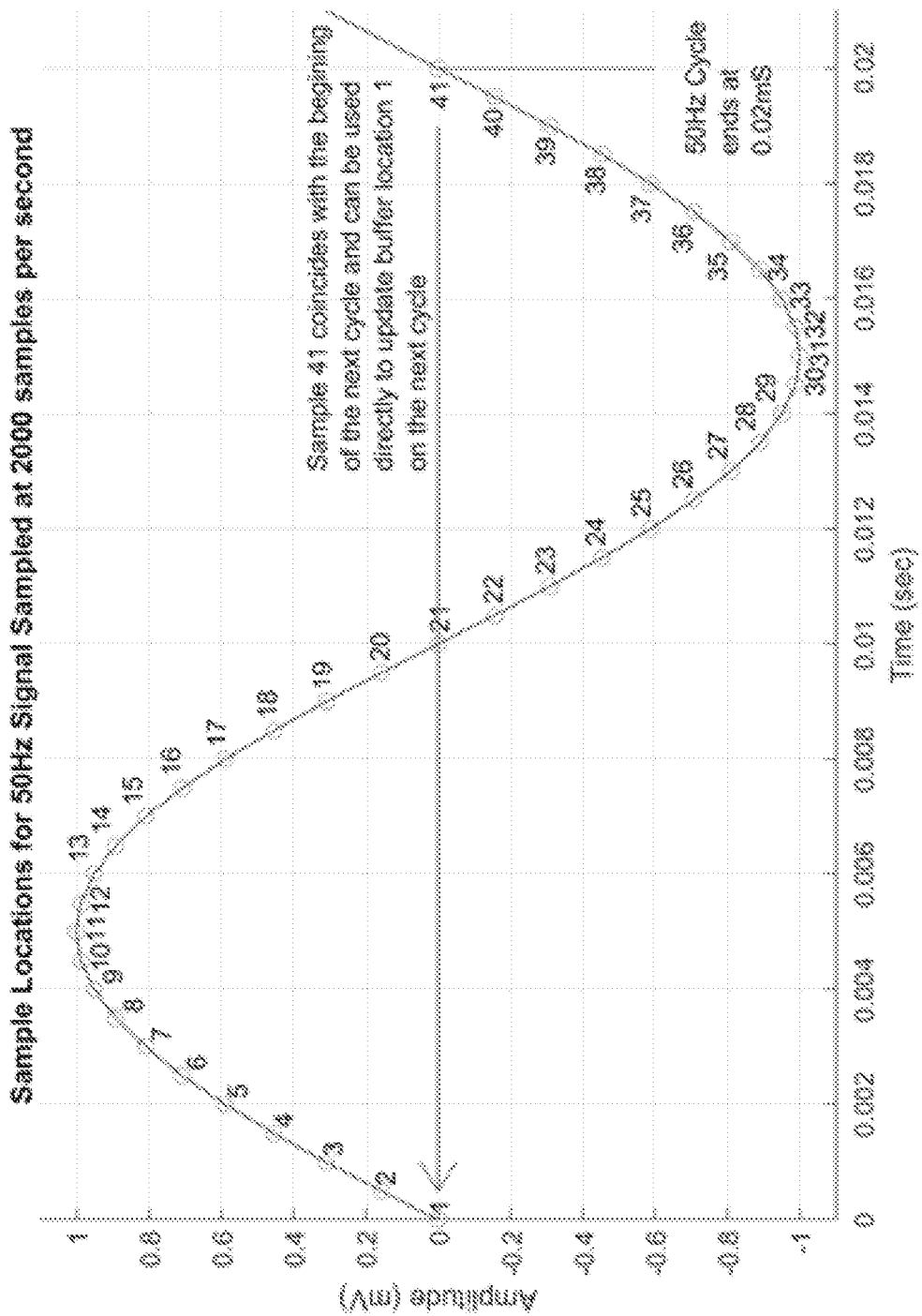
FIG. 7 illustrates an example of a universal notch filter that filters a signal with a 50 Hz interfering signal, according to some embodiments.

In the case of a known 50 Hz interfering signal and a 2000 samples-per-second sample rate, the duration of one cycle of a 50 Hz signal is 40 sample intervals. This can directly fit into the virtual buffer where the cycle duration is an integer number of samples. FIG. 7 illustrates an example of using universal notch filter 102 to filter a signal with a 50 Hz interfering signal sampled at 2000 samples per second, according to some embodiments.

As illustrated in FIG. 7, if sample 1 is at the start of a single cycle, sample data can be added to the virtual buffer sequentially. Sample 41 can be at the end of the 50 Hz cycle (also the beginning of the next cycle). As data samples are added to the virtual buffer, sample 41 can be used to update the data in sample location 1 of the virtual buffer on the next cycle.

Universal notch filter 102 can update sample data in the virtual buffer according to an averaging algorithm that works to accumulate data in the virtual buffer that is at the interference frequency, or some multiple of that frequency. For example, a percentage of sample 41 can be added to a percentage of location 1 in the buffer in the ratio of 0.9 to 0.1. Similarly, the same fraction of sample 42 can be added to location 2 of the buffer, and so on. This approach can be referred to as exponential averaging. Changing the fraction of the incoming signal that is added to the buffer locations can change the convergence rate and sharpness of universal notch filter 102.

The above example of FIG. 7 illustrates a case where the cycle duration is an integer number of samples. But this is often not the case. For example, in the case of a 60 Hz interfering signal and a sample rate of 2000 samples per second, the duration of one cycle of a 60 Hz interfering signal is thirty three and one third (33⅓) sample intervals. This is technologically problematic because 33⅓ ample intervals cannot directly fit into a conventional integral sized buffer.

In some embodiments, this technological problem can be solved through universal notch filter 102's use of a virtual buffer with a length that matches the length of one cycle of the interfering signal. In the case of a 60 Hz interfering signal and a sample rate of 2000 samples, the virtual buffer can be 33⅓ sample intervals in length. Unlike the example case illustrated in FIG. 7, sample 35 may not be able to be directly added to sample 1 after the first cycle. However, sample 35 can theoretically be added to a sample position ⅔ of the distance between virtual memory locations 1 and 2 in the virtual buffer. This can be referred to as virtual memory location 1.67. This situation is illustrated in FIG. 8.

Figure 8:
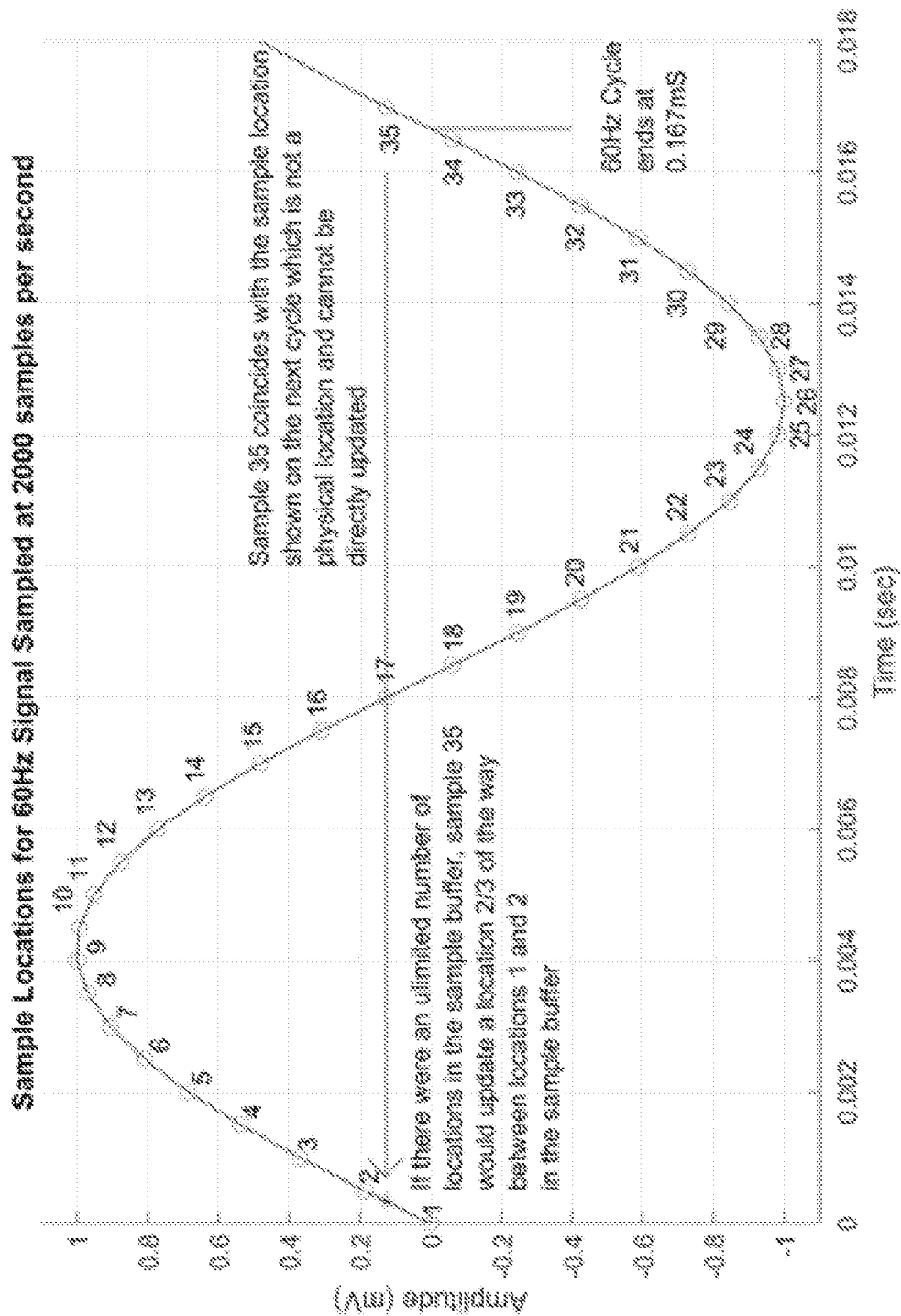
FIG. 8 illustrates an example of a universal notch filter that filters a signal with a 60 Hz interfering signal, according to some embodiments.

As shown in FIG. 8, because there is no physical memory location possible at virtual memory location 1.67, the data from sample 35 can be used to update physical memory locations in the vicinity of virtual memory location 1.67 in the virtual buffer. For example, the values at virtual memory location 1.67 (e.g., sample 35) and virtual memory location 3 can be interpolated to calculate a value at virtual memory location 2 in the virtual buffer, which can then be used to update virtual memory location 2 according to an averaging algorithm (e.g., exponential averaging). Because virtual memory location 2 is one quarter (¼) of the way between location 1.67 and 3, the value at location 2 can be estimated (e.g., using linear interpolation) to be 0.75*value(location 1.67)+0.25*value(location 3). After calculating the estimate, 10% of the estimated value can be added to 90% of the current value at virtual memory location 2 to produce an updated value. Universal notch filter 102 can then repeat this process for the next sample. As part of this process, universal notch filter 102 can continuously update a sample location variable that tracks exactly where the next incoming sample will go in the virtual buffer.

As would be appreciated by a person of ordinary skill in the art, the above is merely an example. As would be appreciated by a person of ordinary skill in the art, there are numerous other interpolation methods involving two or more values to estimate the value at one or more physical memory locations of the virtual buffer. These methods can include, but are not limited to, linear interpolation, quadratic interpolation, polynomial interpolation, splines, and least squares. Moreover, as would be appreciated by a person of ordinary skill in the art, there are numerous averaging methods to update physical memory locations in the virtual buffer to converge to an accurate representation of the interfering signal. These methods can include, but are not limited to, exponential averaging, N-sample averaging, splines, and filtering.

The next part of the process can be to subtract a stored replica of the interfering signal stored in the virtual buffer from the input signal. In the case of an integral number of samples in the interfering signal cycle, the interference can be subtracted from the input signal on a sample by sample basis using the virtual buffer as a circular buffer and wrapping around the end point to go back to the beginning at the end of each cycle.

However, with a non-integral number of samples and the virtual buffer, data is retrieved from virtual memory locations that may not coincide with physical memory locations. In this case, virtual memory locations that are not physical memory locations can be calculated by interpolating values from the known positions. For example, universal notch filter 102 can calculate virtual memory location 4.6 using the average of virtual memory locations 4 and 5, or use higher order interpolations involving more locations as would be appreciated by a person of ordinary skill in the art.

In some embodiments, universal notch filter 102 can increase the number of virtual memory locations in the virtual buffer. Instead of separating the virtual memory locations by one sample interval, universal notch filter 102 can separate by ½ a sample interval (e.g., 2× number of virtual memory locations), ⅓ (e.g., 3× number of virtual memory locations), or any number large enough to accurately represent a single cycle of the interfering signal as long as universal notch filter 102 can track the positions accurately relative to the cycle time. This can allow universal notch filter 102 to increase the accuracy of the representation of the interfering signal cycle and provide better filter performance.

Figure 9:
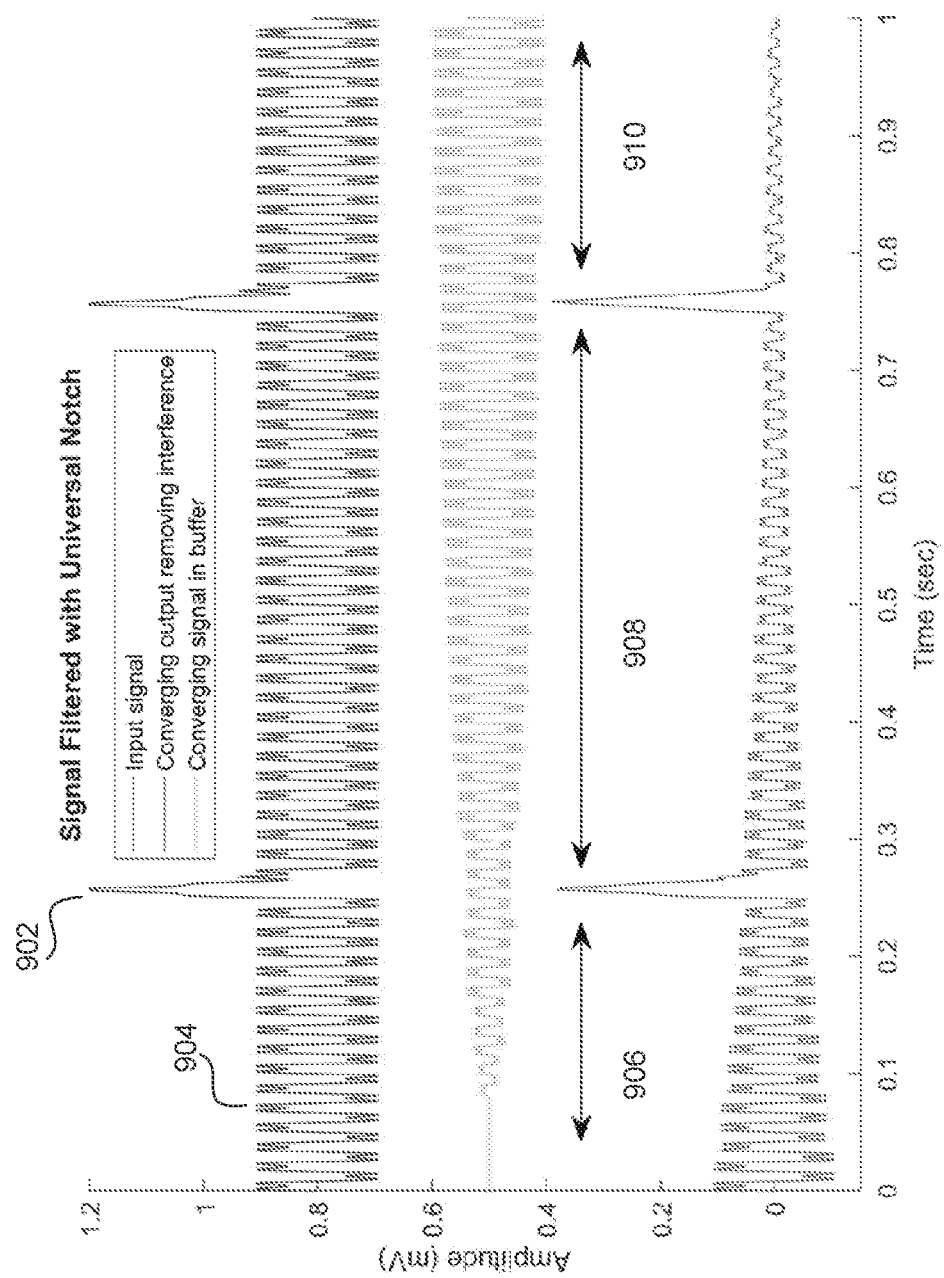
FIG. 9 illustrates an example of a universal notch filter that accumulates a copy of an interfering signal during quiet times, according to some embodiments.

To accumulate the steady state interfering signal in the virtual buffer, data can be gathered during the "quiet times" of the waveforms. As would be appreciated by a person of ordinary skill in the art, a quiet time can be a period of time in the input signal where there are no large spikes or edges. Quiet times can be determined by calculating the slope, magnitude or other measure of signal power, of the input signal, for example. FIG. 9 illustrates an example of universal notch filter 102 that accumulates a copy of an interfering signal during quiet times for an input signal 902, according to some embodiments. Multiple cycles of interfering signal 904 can be gathered in a buffer during a quiet times 906, 908 and 910. These cycles are averaged during the quiet times to build up an accurate copy of the interference 904. Because the interfering signal is constant for segments 906, 908, 910, only cycles of the fundamental frequency and harmonic frequencies can accumulate. Cycles of other frequencies can average out to zero.

For each new point that is sampled from the incoming data, a determination can be made to decide if it is in the "quiet time" of the input signal. A quiet time can be determined by calculating a non-quiet characteristic such as slope, magnitude, power, or various other characteristics of the input signal as would be appreciated by a person of ordinary skill in the art. For example, if the non-quiet characteristic is below a threshold value, a quiet time can be determined to have begun. If the new point is in a quiet time, it can be averaged with the previously stored data at that virtual memory location in the virtual buffer. As time progresses, this averaging process can accumulate a replica of the interfering signal which can be subtracted from the input signal. For those locations that are not in a quiet time, the virtual buffer is not be updated, but the accumulated signal can still be subtracted.

Figure 10:
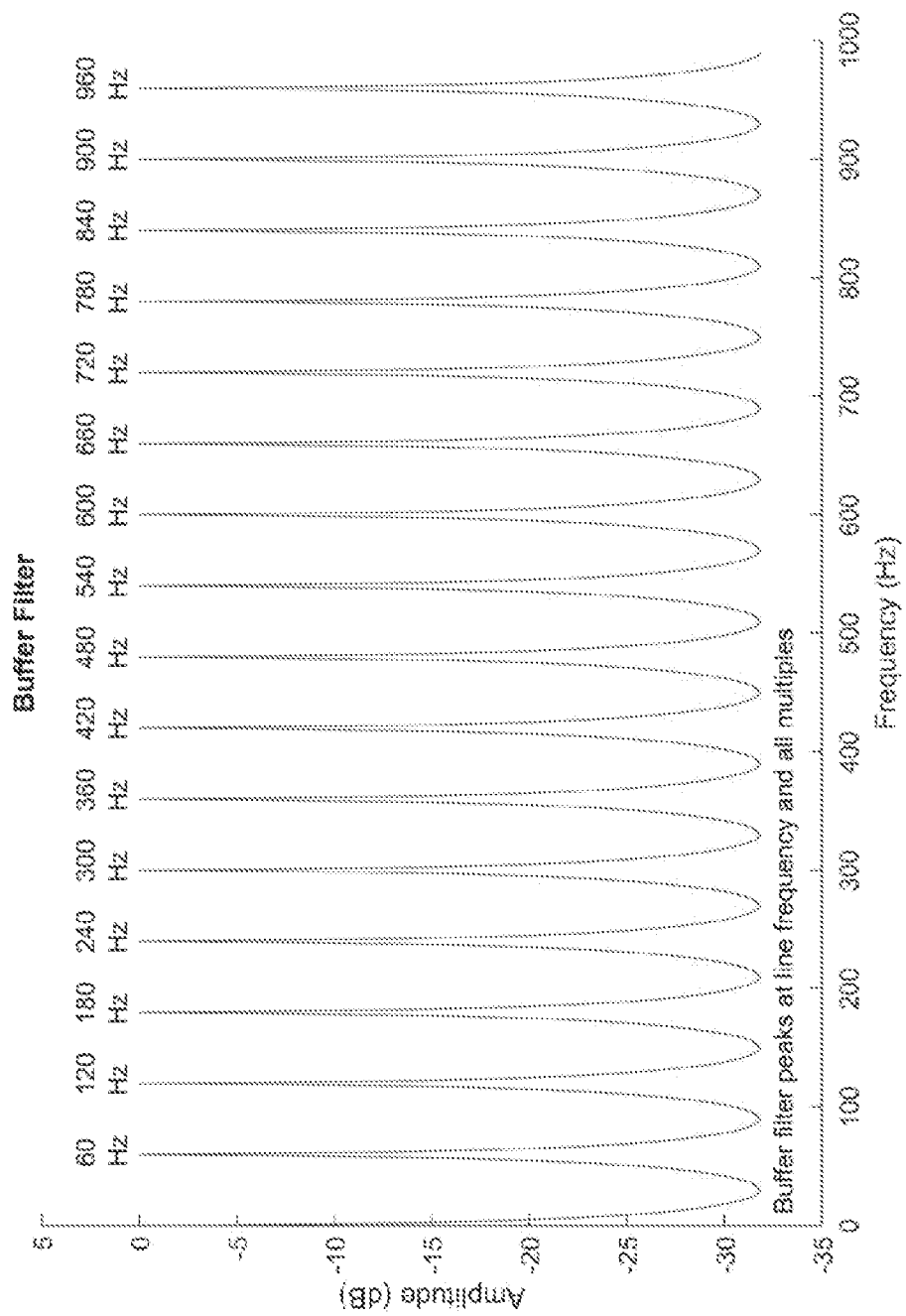
FIG. 10 illustrates an example of the filter response of a universal notch filter that is used to accumulate a copy of an interfering signal, according to some embodiments.

As illustrated in FIG. 10, as each sample is added to the virtual buffer, the averaging can result in a filter that peaks at the interfering frequency 1002 and all harmonics. This can selectively accumulate the interfering frequency and all harmonics and reject all other frequencies so that universal notch filter 102 only subtracts the interfering signal.

FIG. 10 illustrates an example of the filter response of universal notch filter 102 that is used to accumulate a copy of an interfering signal, according to some embodiments. To produce the virtual buffer filter shown in FIG. 10, 5% of the new sample can be added to 95% of the accumulated value to update the virtual buffer, for example. In implementation specific situations, other combined percentages of each new sample and the accumulated value can be combined.

Universal notch filter 102 offers several advantages over conventional notch filters. First, universal notch filter 102 can be flexible. Because the filter frequency is not limited to a discrete number of sample intervals due to the use of a virtual buffer, the choice of filter frequency is virtually unlimited (e.g., within the Nyquist limit of the sampled data). For example, if the nominal 50 power line frequency is slightly off, e.g., 50.001 Hz, universal notch filter 102 can be set to 50.001 Hz to optimize rejection.

Second, universal notch filter 102 can perform tracking of the frequency of the interfering signal. If the frequency of the interfering signal is slowly varying, universal notch filter 102 can track it in real time. Universal notch filter 102 can calculate the frequency of the interfering signal in real time (e.g., using Fast Fourier Transform or other techniques) and adjust the virtual buffer length to match the changing cycle length of the noise signal. Universal notch filter 102 can also check the movement of the stored noise signal. When the virtual buffer cycle length is adjusted to perfectly match the noise cycle length, the stored pattern can be stationary in the virtual buffer. But if the virtual buffer cycle length is too long, the pattern can move to the left. If it is too short, the pattern can move to the right. Therefore, by determining the speed and direction of the pattern shift, universal notch filter 102 can adjust the virtual buffer length to match the cycle length of the interfering signal in the incoming sampled input signal.

Third, universal notch filter 102 can have a fast convergence time. Universal notch filter 102 can modify the averaging mechanism to adjust the convergence time. When it is first turned on, more feedback from the input samples to the storage locations can allow universal notch filter 102 to converge more rapidly. After it has converged, universal notch filter 102 can reduce the feedback percentage to increase the stability of the filter and reject transients from producing artifacts in the output signal.

Finally, universal notch filter 102 can increase the number of virtual memory locations in the virtual buffer. Instead of separating the virtual memory locations by one sample interval, universal notch filter 102 can separate by ½ a sample interval (e.g., 2× number of locations), ⅓ (e.g., 3× number of locations), or any larger number as long as universal notch filter 102 can track the positions accurately relative to the cycle time. This can universal notch filter 102 to increase the accuracy of the representation of the interfering signal cycle and provide better filter performance.

Figure 11:
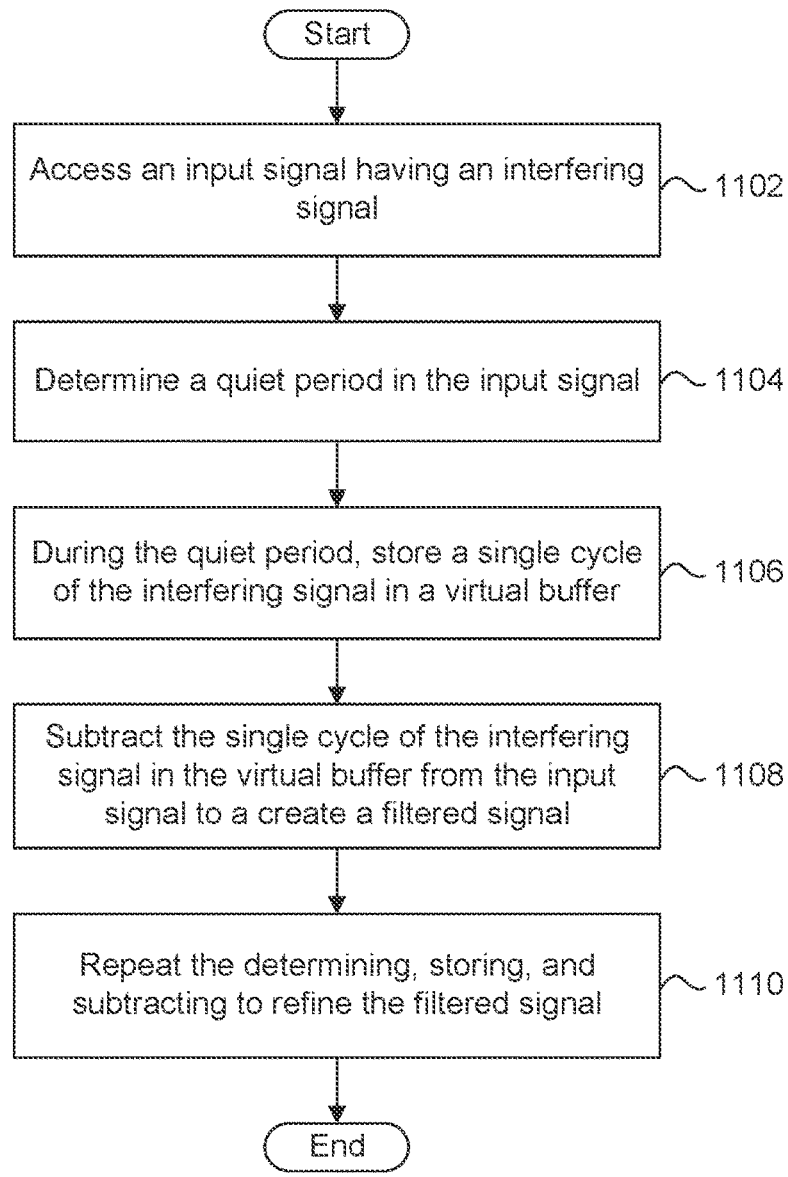
FIG. 11 is a flowchart for a process for using a universal notch filter to filter noise from an input signal, according to some embodiments.

FIG. 11 is a flowchart for a method 1100 for using universal notch filter 102 to filter a fixed frequency interfering signal from an input signal, according to some embodiments. Method 1100 shall be described with reference to FIG. 1. However, method 1100 is not limited to that example embodiment.

In 1102, universal notch filter 102 accesses an input signal comprising a fixed frequency interfering signal. The fixed frequency interfering signal can be an interfering signal having a fixed frequency. The fixed frequency interfering signal can also be an interfering signal having a frequency that varies by approximately 1% over a fixed time period, including, but not limited to, a period of one minute. In other words, the frequency of the interfering signal can be substantially constant.

In 1104, universal notch filter 102 determines a quiet period in the input signal. Universal notch filter 102 can determine the quiet period by calculating a slope of the input signal. Universal notch filter 102 can then determine a presence of the quiet period based on the calculated slope being below a threshold value. Universal notch filter 102 can also determine the quiet period based on magnitude, power, or various other characteristic of the input signal as would be appreciated by a person of ordinary skill in the art.

In 1106, during the quiet period, universal notch filter 102 stores samples of interfering signal in a virtual buffer. Universal notch filter 102 can set the virtual buffer to a length that matches the length of one cycle of the interfering signal. The time at which each new input sample is received is mapped into a virtual memory location in the virtual buffer, and this virtual memory location and the value of the input sample is used to estimate the input value at physical memory locations of the virtual buffer that are in the vicinity of the virtual memory location.

As part of storing, universal notch filter 102 can average a sample of the input signal (e.g., adjusted to be an estimated value at a physical memory location) with a corresponding sample of the interfering signal in the virtual buffer to create an average sample. Universal notch filter 102 can then replace the corresponding sample of interfering signal in the virtual buffer with the average sample.

If there is no physical memory location in the virtual buffer for a sample (e.g., only a virtual memory location exists), the data from the sample can be used to update physical memory locations in the vicinity of virtual memory location of the sample in the virtual buffer. For example, the values at a virtual memory location 1.67 (e.g., sample 35) and virtual memory location 3 can be interpolated to calculate a value at virtual memory location 2 in the virtual buffer, which can then be used to update virtual memory location 2 according to an averaging algorithm (e.g., exponential averaging). Because location 2 is ¼ of the way between virtual memory locations 1.67 and 3, the value at virtual memory location 2 can be estimated (e.g., using linear interpolation) to be 0.75*value(location 1.67)+0.25*value(location 3). After calculating the estimate, 10% of the estimated value can be added to 90% of the current value at virtual memory location 2 to produce an updated value. Universal notch filter 102 can then repeat this process for the next sample. As part of this process, universal notch filter 102 can continuously update a sample location variable that tracks exactly where the next incoming sample will go in the virtual buffer.

In 1108, universal notch filter 102 subtracts the samples from a single cycle of the interfering signal in the virtual buffer from the input signal to create a filtered signal. The subtracting can remove a first harmonic frequency and various other harmonic frequencies from the input signal while avoiding introducing transient responses (e.g., ringing) in the filtered signal. For example, the first harmonic frequency can be 60 Hz and the second harmonic frequency can be 120 Hz or 180 Hz.

In 1110, universal notch filter 102 repeats 1104 to 1108 to refine the filtered signal. As would be appreciated by a person of ordinary skill in the art, samples can be anywhere in the cycle.

Figure 12:
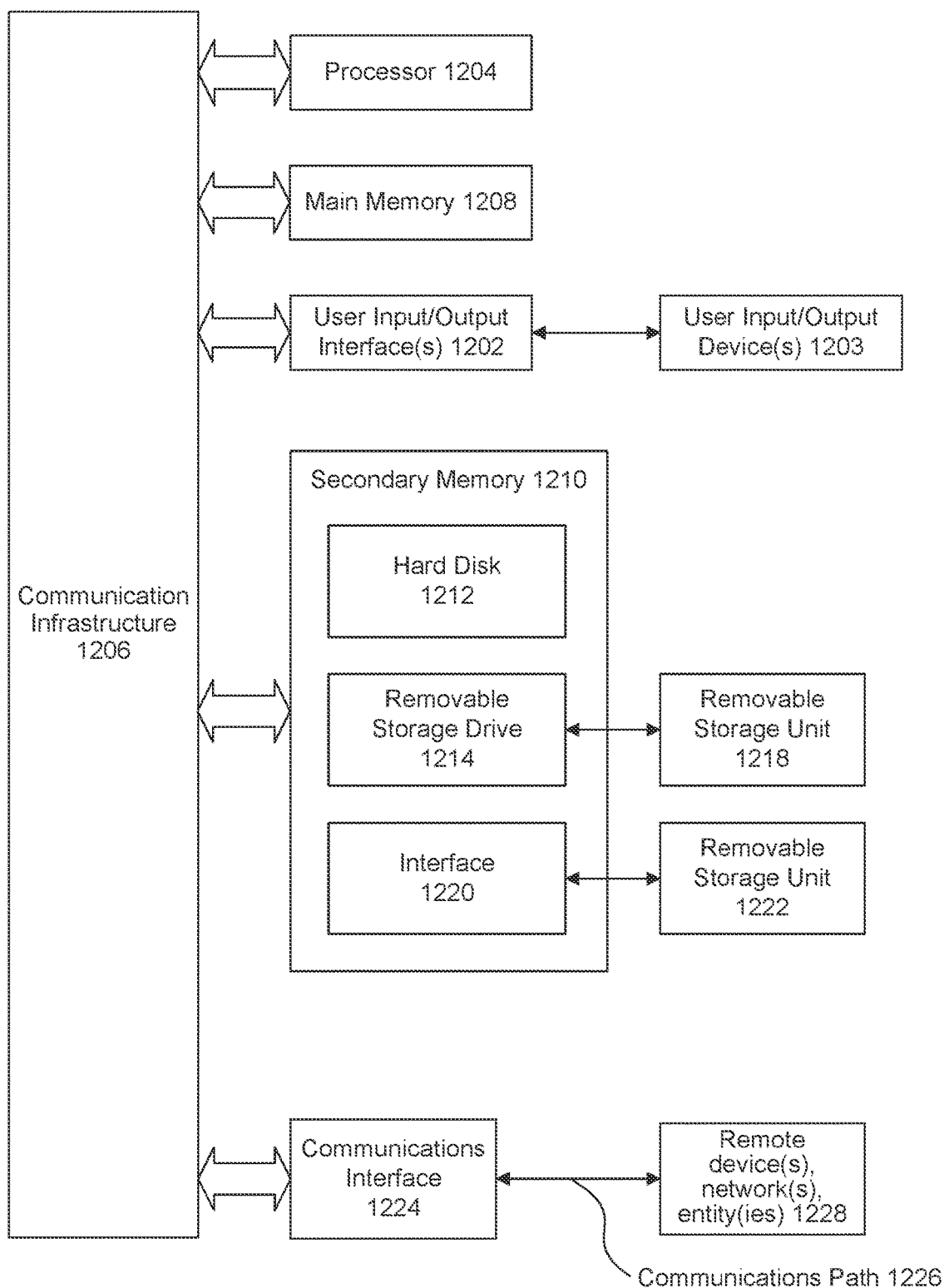
FIG. 12 illustrates an example computer system, according to some embodiments.

Various embodiments can be implemented, for example, using one or more well-known computer systems, such as computer system 1200 shown in FIG. 12. One or more computer systems 1200 can be used, for example, to implement any of the embodiments discussed herein, as well as combinations and sub-combinations thereof.

Computer system 1200 can include one or more processors (also called central processing units, CPUs, or microprocessors), such as a processor 1204. Processor 1204 can be connected to a communication infrastructure or bus 1206.

Computer system 1200 can also include user input/output device(s) 1203, such as monitors, keyboards, pointing devices, etc., which can communicate with communication infrastructure 1206 through user input/output interface(s) 1202.

One or more of processors 1204 can be a graphics processing unit (GPU). In an embodiment, a GPU can be a processor that is a specialized electronic circuit designed to process mathematically intensive applications. The GPU can have a parallel structure that is efficient for parallel processing of large blocks of data, such as mathematically intensive data common to computer graphics applications, images, videos, etc.

Computer system 1200 can also include a main or primary memory 1208, such as random access memory (RAM). Main memory 1208 can include one or more levels of cache. Main memory 1208 can have stored therein control logic (e.g., computer software) and/or data.

Computer system 1200 can also include one or more secondary storage devices or memory 1210. Secondary memory 1210 can include, for example, a hard disk drive 1212 or a removable storage device or drive 1214. Removable storage drive 1214 can be a floppy disk drive, a magnetic tape drive, a compact disk drive, an optical storage device, tape backup device, cloud storage, distributed or RAID storage, or any other storage device/drive/methodology.

Removable storage drive 1214 can interact with a removable storage unit 1218.

Removable storage unit 1218 can include a computer usable or readable storage device having stored thereon computer software (control logic) or data. Removable storage unit 1218 can be a floppy disk, magnetic tape, compact disk, DVD, optical storage disk, or any other computer data storage device. Removable storage drive 1214 can read from or write to removable storage unit 1218.

Secondary memory 1210 can include other means, devices, components, instrumentalities, or other approaches for allowing computer programs or other instructions or data to be accessed by computer system 1200. Such means, devices, components, instrumentalities, or other approaches can include, for example, a removable storage unit 1222 and an interface 1220. Examples of the removable storage unit 1222 and the interface 1220 can include a program cartridge and cartridge interface (such as that found in video game devices), a removable memory chip (such as an EPROM or PROM) and associated socket, a memory stick and USB port, a memory card and associated memory card slot, or any other removable storage unit and associated interface.

Computer system 1200 can further include a communication or network interface 1224. Communication interface 1224 can enable computer system 1200 to communicate and interact with any combination of external devices, external networks, external entities, etc. (individually and collectively referenced by reference number 1228). For example, communication interface 1224 can allow computer system 1200 to communicate with external or remote devices 1228 over communications path 1226, which can be wired or wireless (or a combination thereof), and which can include any combination of LANs, WANs, the Internet, etc. Control logic or data can be transmitted to and from computer system 1200 via communications path 1226.

Computer system 1200 can also be any of a personal digital assistant (PDA), desktop workstation, laptop or notebook computer, netbook, tablet, smart phone, smart watch or other wearable, appliance, part of the Internet-of-Things, or embedded system, to name a few non-limiting examples, or any combination thereof.

Computer system 1200 can be a client or server, accessing or hosting any applications or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); or a hybrid model including any combination of the foregoing examples or other services or delivery paradigms.

Any applicable data structures, file formats, and schemas in computer system 1200 can be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML User Interface Language (XUL), or any other functionally similar representations alone or in combination. Alternatively, proprietary data structures, formats or schemas can be used, either exclusively or in combination with known or open standards.

In some embodiments, a tangible, non-transitory apparatus or article of manufacture including a tangible, non-transitory computer useable or readable medium having control logic (software) stored thereon can also be referred to herein as a computer program product or program storage device. This includes, but is not limited to, computer system 1200, main memory 1208, secondary memory 1210, and removable storage units 1218 and 1222, as well as tangible articles of manufacture embodying any combination of the foregoing. Such control logic, when executed by one or more data processing devices (such as computer system 1200), can cause such data processing devices to operate as described herein.

Based on the teachings contained in this disclosure, it will be apparent to persons skilled in the relevant art how to make and use embodiments of this disclosure using data processing devices, computer systems, or computer architectures other than that shown in FIG. 12. In particular, embodiments can operate with software, hardware, and/or operating system implementations other than those described herein.

What is claimed is:

1. A universal notch filter comprising:
   a memory configured to store a virtual buffer having virtual memory locations; and
   at least one processor coupled to the memory and configured to:
   access an input signal having an interfering signal;
   determine a quiet period in the input signal;
   update, during the quiet period, samples of the interfering signal in the virtual memory locations of the virtual buffer; and
   subtract the samples from a single cycle of the interfering signal in the virtual buffer from the input signal to create a filtered signal, wherein the subtracting removes the interfering signal from the input signal.

2. The universal notch filter of claim 1, wherein the at least one processor is further configured to:
   calculate a non-quiet characteristic of the input signal; and
   determine if the non-quiet characteristic is below a threshold value, thereby determining a presence of the quiet period.

3. The universal notch filter of claim 1, wherein the updating by the at least one processor comprises:
   averaging a sample of the input signal with a corresponding sample of the interfering signal in the virtual buffer to create an average sample; and
   replacing the corresponding sample of the interfering signal in the virtual buffer with the average sample.

4. The universal notch filter of claim 3, wherein the averaging comprises addition of a percentage of the input signal with a percentage of the corresponding sample of the interfering signal in the virtual buffer.

5. The universal notch filter of claim 1, wherein the updating by the at least one processor comprises:
   updating a physical memory location in the virtual buffer based on a sample of the interfering signal, wherein the sample of the interfering signal corresponds to a non-physically addressable memory location for the virtual buffer.

6. The universal notch filter of claim 1, wherein a frequency of the interfering signal of the input signal is substantially constant.

7. The universal notch filter of claim 1, wherein the processor is further configured to set a length of the virtual buffer to match a length of one cycle of a frequency of the interfering signal.

8. A non-transitory computer-readable medium having instructions stored thereon that, when executed by at least one computing device, cause the at least one computing device to perform operations comprising:
   accessing an input signal having an interfering signal;
   determining a quiet period in the input signal;
   updating, during the quiet period, samples of the interfering signal in virtual memory locations of a virtual buffer; and
   subtracting the samples from a single cycle of the interfering signal in the virtual buffer from the input signal to create a filtered signal, wherein the subtracting removes the interfering signal from the input signal.

9. The non-transitory computer-readable medium of claim 8, wherein the determining comprises:
   calculating a non-quiet characteristic of the input signal; and
   determining the non-quiet characteristic is below a threshold value, thereby determining a presence of the quiet period.

10. The non-transitory computer-readable medium of claim 8, wherein the updating comprises:
    averaging a sample of the input signal with a corresponding sample of the interfering signal of the input signal in the virtual buffer to create an average sample; and
    replacing the corresponding sample of the interfering signal in the virtual buffer with the average sample.

11. The non-transitory computer-readable medium of claim 10, wherein the averaging comprises addition of a percentage of the input signal with a percentage of the corresponding sample of the interfering signal in the virtual buffer.

12. The non-transitory computer-readable medium of claim 8, wherein the updating comprises:
    updating a physical memory location in the virtual buffer based on a sample of the interfering signal, wherein the sample of the interfering signal corresponds to a non-physically addressable memory location for the virtual buffer.

13. The non-transitory computer-readable medium of claim 8, wherein a frequency of the interfering signal of the input signal is substantially constant.

14. The non-transitory computer-readable medium of claim 8, wherein the operations further comprise:
    setting a length of the virtual buffer to match a length of one cycle of a frequency of the interfering signal.

15. A computer-implemented method for filtering an input signal to create a filtered signal, comprising:
    accessing an input signal having an interfering signal;
    determining a quiet period in the input signal;
    updating, during the quiet period, samples of the interfering signal in virtual memory locations of a virtual buffer; and
    subtracting the samples from a single cycle of the interfering signal in the virtual buffer from the input signal to create a filtered signal, wherein the subtracting removes the interfering signal from the input signal.

16. The computer-implemented method of claim 15, further comprising:

calculating a non-quiet characteristic of the input signal; and determining if the non-quiet characteristic is below a threshold value, thereby determining a presence of a quiet period.

17. The computer-implemented method of claim 15, wherein the updating comprises:

averaging a sample of the input signal with a corresponding sample of the interfering signal in the virtual buffer to create an average sample; and replacing the corresponding sample of the interfering signal in the virtual buffer with the average sample.

18. The computer-implemented method of claim 17, wherein the averaging comprises addition of a percentage of the input signal with a percentage of the corresponding sample of the interfering signal in the virtual buffer.

19. The computer-implemented method of claim 15, wherein the updating comprises:

updating a physical memory location in the virtual buffer based on a sample of the interfering signal, wherein the sample of the interfering signal corresponds to a non-physically addressable memory location for the virtual buffer.

20. The computer-implemented method of claim 15, wherein a frequency of the interfering signal of the input signal is substantially constant.

\* \* \* \* \*